United States Patent [19]
Castle

[11] Patent Number: 5,197,961
[45] Date of Patent: Mar. 30, 1993

[54] TOENAIL EXTENDER

[76] Inventor: Tris S. Castle, 2652 S. Cottonwood Dr., Tempe, Ariz. 85282

[21] Appl. No.: 889,614

[22] Filed: May 12, 1992

[51] Int. Cl.⁵ .................... A45D 29/00; A45D 31/00
[52] U.S. Cl. ........................................ 606/1; 128/898; D28/56; D28/57
[58] Field of Search .................. 128/898; D28/56–62; 222/135, 137, 145, 386; 606/1, 108; 221/96, 268

[56] References Cited
U.S. PATENT DOCUMENTS

| | | | |
|---|---|---|---|
| 155,108 | 9/1849 | Rucker | D28/57 |
| 307,106 | 4/1890 | Krebs | D28/57 |
| 3,323,682 | 6/1967 | Creighton et al. | 222/137 |
| 3,330,444 | 7/1967 | Raypholtz | 222/137 |

*Primary Examiner*—Stephen C. Pellegrino
*Assistant Examiner*—Glenn Dawson
*Attorney, Agent, or Firm*—Warren F. B. Lindsley

[57] ABSTRACT

A dual purpose prosthetic device for moving a cannula under an ingrown toenail and sequentially positioning and adhesively binding an extender to an edge of the toenail of a patient. The extender is essentially U-shaped in cross-section. The device includes a double-lumen housing and a dual plunger.

6 Claims, 1 Drawing Sheet

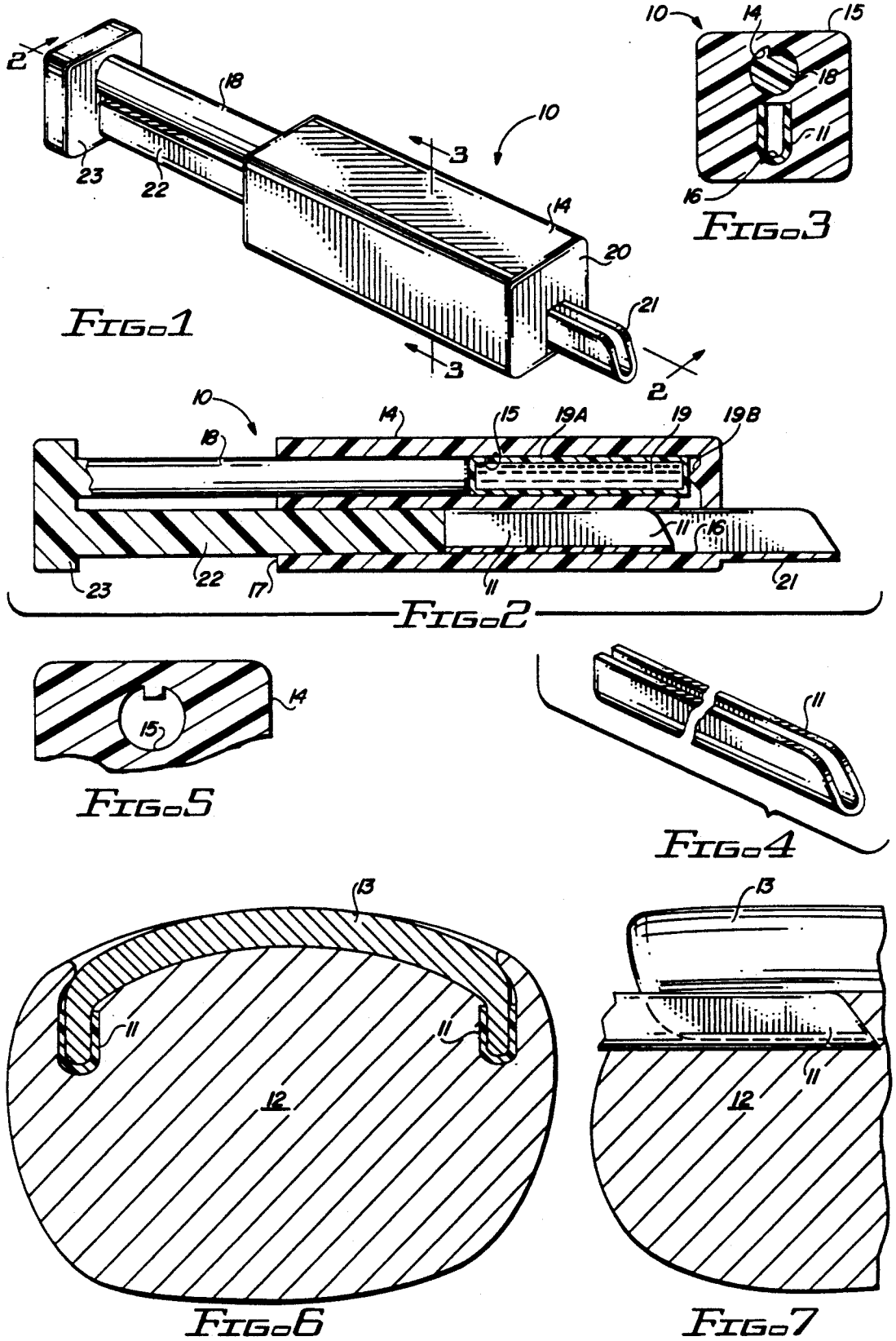

TOENAIL EXTENDER

BACKGROUND OF THE INVENTION

This invention relates to toenails and more particularly to the medical problem of ingrown toenails.

For as long as people have been cutting their toenails, they have been suffering with ingrown toenails. Although not normally considered a serious medical problem, ingrown toenails are quite painful and usually present a problem which lasts for years. In the case of diabetics who are prone to both circulatory problems and severe infections, an ingrown toenail may represent the first stage of a progressive condition which may become life threatening.

DESCRIPTION OF THE PRIOR ART

The treatment for ingrown toenails has gone unchanged for over one hundred years. It has involved removal of the offending nail, which frequently results in the new nail being permanently deformed, trimming of the nail margin which only alleviates the symptoms temporarily and usually results in a recurrence of the condition.

In the past, the only treatment regimen which offered any hope of cure, involved packing sufficient quantities of cotton between the nail and nail bed to allow the nail to grow over, rather than into, the end of the toe.

Unfortunately, this treatment resulted in the patient packing his or her toenails daily which was both time consuming and painful. It called for more patience, care, and attention to details than patients were willing to accept. Therefore, they would simply clip their nail thus starting the entire medical problem over again.

The anatomy of the problem is simple. Unlike finger nails which grow with only a slight convexity, toenails have a distinct vertical margin on each side. When this vertical margin is trimmed shorter than the toe itself, the epidermis fills in the natural groove in which the nail margin used to sit. Therefore, when the nail grows out it grows into, instead of over the end of the toe. Thus, the vertical nail margin acts like a foreign body, causing a puncture wound and infection.

SUMMARY OF THE INVENTION

The solution to the problem is to find a way to recreate the channel in which the vertical nail margin grows which would be sustained for a sufficient length of time to allow the nail to grow out over the end of the toe. To insure patient compliance, this must be done with a minimum of discomfort and inconvenience to the patient.

All of the above goals could be met by inserting a small, "U"-shaped, prosthetic device between the toe and the toenail which would extend out past the end of the toe. If this nail extender were attached to the toenail itself, it would migrate anteriorly as the natural nail grows.

It is, therefore, one object of this invention to provide a new and improved prosthetic device for treating ingrown toenails.

Another object of this invention is to provide a new and improved channel for positioning on the toe within which the nail margin may grow.

A further object of this invention is to provide a new and improved appliance for positioning a U-shaped prosthetic device between the toe and toenail.

Further objects and advantages of the invention will become apparent as the following description proceeds and the features of novelty which characterize the invention will be pointed out with particularity in the claims annexed to and forming a part of this specification.

BRIEF DESCRIPTION OF THE DRAWING

The present invention may be more readily described with reference to the accompanying drawing, in which:

FIG. 1 is a perspective view of a prosthetic device embodying the invention;

FIG. 2 is a cross sectional view of FIG. 1 taken along the line 2—2;

FIG. 3 is a cross sectional view of FIG. 1 taken along the line 3—3;

FIG. 4 is a perspective view of the toenail extender shown in FIG. 2;

FIG. 5 is a cross sectional view of FIG. 2 showing the cavity for receipt of an adhesive;

FIG. 6 is an enlarged cross sectional view of a toe and toenail with the extender in place; and FIG. 7 is a cross sectional lateral view of the toe, toenail and extender in place.

DESCRIPTION OF THE PREFERRED EMBODIMENT

Referring more particularly to the drawing by characters of reference, FIGS. 1-5 disclose a prosthetic device 10 for placing an extender 11 between a toe 12 and toenail 13, as shown in FIGS. 6 and 7. This prosthetic device comprises a housing 14 defining two longitudinally extending cavities, openings or channels 15 and 16 with channel 15 receiving in end 17 of housing 14 and longitudinally thereof a plunger 18 for moving a suitable medication and/or adhesive 19 or a mixture thereof packaged in a container 19A against a sharp point 19B at the end of channel 15. This adhesive may be, for example, a permanent, non-toxic, waterproof adhesive with a short drying time. The adhesive now used for attaching artificial fingernails may be used.

Channel 16 at end 20 of housing 14 comprises a cannula 21 which projects outwardly of and forms a part of housing 14. This cannula is an inverted U-shaped channel extension for channel 16 extending longitudinally outwardly of housing 14. Channel 16 and its extension formed by cannula 21 provides a track for extender 11 which is arranged to be pushed by plunger 22 through channel 16 and cannula 21 underneath the edge of a toenail as hereinafter explained.

As noted from FIGS. 1 and 2, plungers 18 and 22 comprise a single structure secured together by a handle 23 and move in unison into and out of channels 15 and 16. Handle 23 formed of a suitable plastic material is large enough to be comfortable in a practitioner's hand and still allow sufficient grip to force the cannula between the nail and nail bed of the patient. Channels 15 and 16 of housing 14 should be large enough to contain adhesive 19 and nail extender 11, respectively, for simultaneous application so as to reduce the steps of treatment to a minimum.

Extender 11 is usually formed of a thin, firm, flexible plastic material which may be cut or filed without splitting. The material now used for making artificial fingernails could be used for manufacturing these extenders.

Thus, the prosthetic device 10 comprises a dual purpose medical instrument for forcing a cannula between an edge of a toenail and the toe to retrieve the edge of a toenail from its position in the flesh of the toe and then to sequentially force an extender 11 over and along the edge of the toenail together with a medication and/or adhesive for attaching and holding the extender on or to the toenail.

In order to properly use the disclosed prosthetic device, the following steps should be followed:

1. Provide adequate anesthesia to the patient by a digital block with 2% Lidocaine.

2. Provide a 15 minute soak of the toe in Betadine. This should provide adequate time for the digital block to take effect.

3. Using proper aseptic technique, grasp the handle and force the cannula between the nail and the nail bed.

4. While holding the handle of device 10 firmly with one hand, press plunger 22 with the other hand thereby forcing adhesive 19 into the groove of nail extender 11 and the nail extender into the channel created by cannula 21.

5. While continuing to apply pressure to plunger 22, withdraw the cannula from the toe leaving extender 11 under the edge of the toenail.

6. Allow adequate drying time of the adhesive while firm pressure is applied to the toe to stop any minor bleeding that may be present and to adhere the extender to the edge of the toenail.

7. Clip away any excess nail extender with the nail extender protruding ¼ inch past the end of the toe.

8. Apply a dry, sterile dressing to the toe for comfort and protection.

9. Use analgesics (Tylenol #3 or Darvocet) if needed for pain relief for approximately 48 hours after treatment.

10. Schedule a follow-up appointment in two to three days to check for proper placement of the extender and to note and treat any infection.

11. Instruct the patient to NEVER AGAIN cut his or her toenails shorter than the end of the toe.

12. Repeat the same process for the other edge of the toenail if necessary.

Although but one embodiment of the invention has been shown and described, it will be apparent to those skilled in the art that various changes and modifications may be made therein without departing from the spirit of the invention or from the scope of the appended claims.

What is claimed is:

1. A dual purpose prosthetic device for treating ingrown toenails comprising:

a housing, a pair of channels extending longitudinally in said housing, said housing having a cannula extending outwardly thereof from one end of one of said channels, said cannula comprising a track for receiving therein a nail extender, the other of said channels being provided for receiving an adhesive, means for providing an opening from said other of said channels into said one of said channels for movement of said adhesive therethrough, a nail extender for positioning in said one of said channels within said housing, and plunger means for simultaneously moving said extender positioned in said housing in said one of said channels into said cannula and an adhesive from said other of said channels into said extender.

2. The dual purpose prosthetic device set forth in claim 1 wherein:

said cannula comprises a U-shaped configuration, and said extender comprises a U-shaped configuration similar to but smaller than said cannula for fitting into said cannula in the same orientation and movement therealong.

3. The dual purpose prosthetic device set forth in claim 2 wherein:

said one of said channels opens outwardly of said housing at its end opposite to said cannula for receipt of said extender.

4. The dual purpose prosthetic device set forth in claim 1 wherein:

said plunger means comprises a pair of plungers one for each channel.

5. The dual purpose prosthetic device set forth in claim 1 wherein:

said extender comprises a thin, flexible plastic material.

6. A process for treating ingrown toenails comprising the steps of:

forcing a cannula underneath and along the edge of a toenail, moving an extender into said cannula while said cannula is positioned along the edge of the toenail, and simultaneously with the movement of said extender into said cannula dispersing an adhesive into said extender for causing said extender to adhere to said toenail.

* * * * *